United States Patent
Ogisu et al.

(10) Patent No.: US 7,176,448 B2
(45) Date of Patent: Feb. 13, 2007

(54) DAMAGE DETECTION SYSTEM FOR STRUCTURAL COMPOSITE MATERIAL AND METHOD OF DETECTING DAMAGE TO STRUCTURAL COMPOSITE MATERIAL

(75) Inventors: Toshimichi Ogisu, Tokyo (JP); Masakazu Shimanuki, Tokyo (JP); Nobuo Takeda, Saitama (JP)

(73) Assignee: Fuji Jukogyo Kabushiki Kaisha, Tokyo (JP)

( * ) Notice: Subject to any disclaimer, the term of this patent is extended or adjusted under 35 U.S.C. 154(b) by 208 days.

(21) Appl. No.: 10/947,312

(22) Filed: Sep. 23, 2004

(65) Prior Publication Data

US 2005/0067559 A1    Mar. 31, 2005

(30) Foreign Application Priority Data

Sep. 26, 2003    (JP)    ............... 2003-335108

(51) Int. Cl.
    *G01J 1/04*    (2006.01)
(52) U.S. Cl. .............. 250/227.14; 250/227.16
(58) Field of Classification Search ........... 250/227.14, 250/227.16
    See application file for complete search history.

(56) References Cited

U.S. PATENT DOCUMENTS

| | | | |
|---|---|---|---|
| 5,338,928 A | | 8/1994 | Jamieson et al. |
| 5,814,729 A | | 9/1998 | Wu et al. |
| 6,188,705 B1 | * | 2/2001 | Krainak et al. ............... 372/32 |
| 6,370,964 B1 | | 4/2002 | Chang et al. |
| 7,017,421 B2 | * | 3/2006 | Kehlenbach ................. 73/800 |

FOREIGN PATENT DOCUMENTS

| | | |
|---|---|---|
| JP | 2001-154069 A | 6/2001 |
| JP | 2001-154069 A | 6/2001 |

\* cited by examiner

*Primary Examiner*—Que T. Le
(74) *Attorney, Agent, or Firm*—Birch, Stewart, Kolasch & Birch, LLP (57) ABSTRACT

Damage caused to a structural composite material is detected while reduction in the strength thereof is prevented. A damage detection system 10 for a structural composite material includes a vibration application apparatus 20 including: a sheet body 22; a plurality of piezo elements 21 sprinkled throughout and held by the sheet body 22; and wires 23 for the piezo elements 21 provided to the sheet body 22. The damage detection system 10 also includes: a fiber optic sensor 30 which includes a grating portion 33 in a core portion 32 thereof, the grating portion 33 reflecting light of a predetermined wavelength; a light source to perform light irradiation onto the core portion 32; and a characteristic detection unit 42 to detect a characteristic of the light reflected from the grating portion 33.

29 Claims, 6 Drawing Sheets

SPECTRUM ANALYZER — 42

DAMAGE DETECTION SYSTEM FOR STRUCTURAL COMPOSITE MATERIAL AND METHOD OF DETECTING DAMAGE TO STRUCTURAL COMPOSITE MATERIAL

This Non-provisional application claims priority under 35 U.S.C. § 119(a) on Patent Application No(s). 2003-335108 filed in Japan on Sep. 26, 2003, the entire contents of which are hereby incorporated by reference.

BACKGROUND OF THE INVENTION

1. Field of the Invention

The present invention relates to a damage detection system which detects damage such as defects and aged deterioration caused to a structural composite material applied to aircraft structures, space equipment such as satellites and space stations, high-rise buildings, public infrastructures, high-speed vehicles, and the like. The present invention also relates to a method of detecting damage to the structural composite material.

2. Description of the Related Art

In a field where both strength and weight reduction are required for a material, for example, airframes of aircrafts and the like, it is essential that a composite material such as Carbon Fiber Reinforced Plastics (CFRP) is widely applied in order to meet such requirements.

There has been disclosed, as an inspection apparatus to detect such as damage and defects caused to this kind of composite material, an inspection apparatus which includes film-shaped piezo elements and cables sandwiched between polyimide films (for example, see Patent Document 1: U.S. Pat. No. 6,370,964). This inspection apparatus is installed for inspection by embedding polyimide films having the piezo elements into the composite material of an unfinished structure, or by adhering the films to the surface of a structure with an adhesive. The inspection apparatus detects outputs from the piezo elements which are produced based on vibration applied to the structure, and detects such as damage and defects caused to the structural composite material based on the detected waveforms.

Additionally, detection processing apparatuses of a Fiber Bragg Grating (FBG) type, an Optical Time Domain Refrectable (OTDR) type, and a Fabry-Perot type, in which an optical fiber is used, can be given as examples of other earlier development. As shown in JP-Tokukai-2001-154069A (Patent Document 2), the diameter of an optical fiber is becoming finer and finer (for example, diameter of 52 μm) in recent years, and thus the strength of a structure is not reduced much even with the optical fiber embedded therein. Therefore, an optical fiber has an advantage that there is a high degree of freedom for installation thereof.

According to the earlier development described in Patent Document 1, to use the inspection apparatus, it is required that polyimide films be embedded in the structure or adhered to the structure with an adhesive, as described above. However, the polyimide films are flexible and easy to deform, and thus strength required for a structural material cannot be expected therefrom. Hence, lamination work thereof is complicated and thus increased.

According to the earlier development in which strain and the like of a structural composite material is detected using an optical fiber, influence of installation of the optical fiber, which causes reduction in the strength of a structure, can be suppressed to the minimum if the optical fiber with a fine diameter described in Patent Document 2 is used. However, in the earlier development, it is a local strain change in the vicinity of the optical fiber that what is recognized through inspection. Therefore, there has been a disadvantage that damage cannot be detected unless there is a local strain change.

SUMMARY OF THE INVENTION

An object of the present invention is to detect damage caused to a structural composite material while reduction in the strength of the structural composite material is suppressed.

Another object of the present invention is to detect the location or degree of damage caused to a structural composite material.

A first aspect of the invention is a damage detection system for a structural composite material, comprising: a piezo element; a fiber optic sensor which includes a grating portion in a core portion thereof, the grating portion reflecting light of a predetermined wavelength; a light source to perform light irradiation onto the core portion; and a characteristic detection unit to detect a characteristic of the light reflected from the grating portion.

In the first aspect of the invention, the piezo element may be installed at a portion appearing on the surface of the structural composite material. The way of installation is not limited; however, a way in which the strength of the structural composite material is not reduced, for example, adhesion or bonding, is preferable.

The fiber optic sensor is preferably installed at a damage detection point. For example, the fiber optic sensor may be installed in a region which is too small to directly install therein a sensor that uses a conventional piezo element. Alternatively, the fiber optic sensor may be installed inside a hollow in the structural composite material to which a hole for installation work needs to be provided, or in the vicinity of or within the joining portion between a plurality of members included in the structural composite material. The way of installation is not limited; however, a way in which the strength of the structural composite material is not reduced, for example, adhesion or bonding, is preferable.

Vibration is applied to the structural composite material by applying a driving voltage to the piezo element. Preferably, the piezo element is installed, for example, such that the vibration propagation path from the piezo element to the grating portion passes through a point prone to damage, or passes through a point where damage occurrence should be detected. Vibration to be applied may be continuous vibration; however, instantaneous vibration is preferable. Such vibration is transmitted from the piezo element to the optical fiber through the composite material. The optical fiber is distorted due to the vibration, whereby characteristics of light reflected from the grating portion, for example, wavelength, is shifted.

Here, if damage has been caused to a portion between the piezo element and the grating portion of the fiber optic sensor, the vibration is attenuated while transmitted, and characteristics of reflection light such as frequency detected by the characteristic detection unit is shifted.

Thus, the position of damage is specified based on the position of the grating portion of the fiber optic sensor, and the degree of damage is specified based on the shift in characteristics of reflection light such as frequency detected by the characteristic detection unit.

In the first aspect of the invention, a fiber optic sensor using an optical fiber whose diameter can be made small is used. Since the contact area between the structural composite material and the optical fiber is small, reduction in the strength of the composite material caused by such as separation can be suppressed even when the optical fiber is embedded directly in the material for the structural composite material. Further, when it is required that a hole for installation work be provided, the diameter of the hole can be made small. Therefore, reduction in the strength of the structural composite material can be suppressed. Moreover, when the optical fiber is installed by providing a groove on the surface of the structural composite material, the width of the groove can be made narrow. Therefore, reduction in the strength of the structural composite material can be suppressed. When the structural composite material includes a plurality of members, by using an optical fiber with a fine diameter, reduction in the strength of the structural composite material can be suppressed, and the fiber optic sensor can be placed in the joining (for example, bonding, adhering or fastening) portion to be sandwiched between the members.

Moreover, in the invention, complicated lamination work is not required for installation of the sensor unlike the sensor using the piezo element of the earlier development, and the sensor can therefore be easily installed.

Thus, while reduction in the strength of the structural composite material can be suppressed, damage can be detected at respective points including those where damage is easily caused.

Furthermore, since the fiber optic sensor can detect damage on the vibration transmission path between the vibration generating point and the grating portion, damage detection in a wider area is possible unlike the case of earlier development where damage is detected only around the grating portion.

Preferably, the structural composite material includes a plurality of members which are joined to each other at a joining portion, and the piezo element and the fiber optic sensor are disposed in or in the vicinity of the joining portion.

Generally, to the joining portion between the members of the structural composite material, damage such as delamination or disbanding is sometimes caused, and therefore, damage detection is particularly required. However, in most cases, such a joining portion is generally included inside a structure or in a complex structure. Installation inside a structure or installation of sensors may cause reduction in the strength of the structure, since, for example, a large hole for installation work needs to be provided. Accordingly, damage detection is difficult in general.

In view of this point, using the piezo element and the fiber optic sensor, the fiber optic sensor may be installed at a point in the vicinity of a joining portion where some kinds of sensors are difficult to install, and the piezo element may be provided in the vicinity thereof. The damage detection operation after installation is the same as that of the first aspect of the invention.

In the invention, the piezo element and the fiber optic sensor are placed in or in the vicinity of the joining portion between members of a structure. Hence, even when the joining portion exists inside the structure or in a complex structure, damage such as delamination or disbanding caused to the joining portion can be detected in a preferable manner particularly when the fiber optic sensor is disposed in the vicinity of a joining portion inside the structure or in a complex structure.

Thus, a composite material is applicable even inside a structure or in a complex structure having a joining portion, to which a composite material has not been sufficiently applied due to difficulty in damage detection.

Preferably, the fiber optic sensor is placed in the joining portion so as to be sandwiched between the members, or embedded in one of the members so as to be placed in the vicinity of the joining portion.

As described above, there is a possibility that damage such as delamination or disbanding is caused to a joining portion of the composite material. To detect such damage, a detection unit is preferably provided on the boundary surface of the joining portion between the members. However, if a sensor or the like using a conventional piezo element is disposed on the boundary surface, there is a possibility that the strength of the joining portion is reduced. Therefore, it is preferable that a fiber optic sensor of which an area in contact with the surroundings is easily made small is placed between the boundary surfaces of a joining portion, or embedded on one of the boundary surface sides opposed to each other, whereby reduction in the strength of the joining portion is prevented.

In the invention, the fiber optic sensor whose surface area can be easily made small is sandwiched between the boundary surfaces of a joining portion of the members or embedded in the vicinity of the boundary surface of one of the members. Accordingly, while reduction in the strength of the joining portion is prevented, damage detection can be performed in the nearest vicinity of a point where separation easily occurs. Thus, damage can be detected at an early stage with high accuracy.

Preferably, the piezo element and the fiber optic sensor are disposed such that one of the members is placed therebetween.

Here, damage detection is performed with one of the members placed between the piezo element and the fiber optic sensor. An elastic wave is to be propagated through the entire member when vibration is applied by the piezo element, thereby allowing preferable detection on damage throughout the entire member.

In the invention, the piezo element and the fiber optic sensor are placed to sandwich one of the members. Thus, even when damage such as separation is caused to the entire member sandwiched therebetween, damage can be detected at an early stage with high accuracy. In other words, the entire member sandwiched therebetween serves as a vibration propagation path, and accuracy in damage detection on the entire member can be improved more.

A second aspect of the invention is a damage detection method for a structural composite material, comprising providing: a piezo element fixedly disposed at a predetermined point of the structural composite material; a lead wire which transmits a signal to the piezo element; a fiber optic sensor which is fixedly disposed so as to sandwich, between the piezo element and the fiber optic sensor, a composite material to form the structural composite material, and includes a grating portion in a core portion, the grating portion reflecting light of a predetermined wavelength; a light source to perform light irradiation onto the core portion; and a characteristic detection unit to detect a characteristic of the light reflected from the grating portion. The method also comprises: applying vibration to the structural composite material by using the piezo element; and detecting damage based on a change in an output from the characteristic detection unit.

In the second aspect of the invention, the way of installation of a piezo sensor (piezo element) and the fiber optic sensor may be the same as that of the first aspect of the invention.

The piezo element is placed at an arbitrary point of the structural composite material, and vibration is applied thereto. Preferably, vibration is applied, for example, to a point from which the vibration propagates to the grating portion while passing through a point prone to damage, or passing through a point where damage occurrence should be detected. Vibration to be applied may be continuous vibration; however, instantaneous vibration is preferable. The principle of detecting damage occurrence, the location of the damage occurrence and the degree of the damage based on a detection output for an elastic wave propagated from the grating portion, which detection output is outputted by the characteristic detection unit, may be the same as that of the first aspect of the invention.

From the second aspect of the invention, the same advantageous effects as those of the first aspect can be obtained.

BRIEF DESCRIPTION OF THE DRAWINGS

The present invention will become more fully understood from the detailed description given hereinbelow and the accompanying drawings which are given by way of illustration only, and thus are not intended as a definition of the limits of the present invention, and wherein.

DETAILED DESCRIPTION OF THE PREFERRED EMBODIMENT

Figure 1:
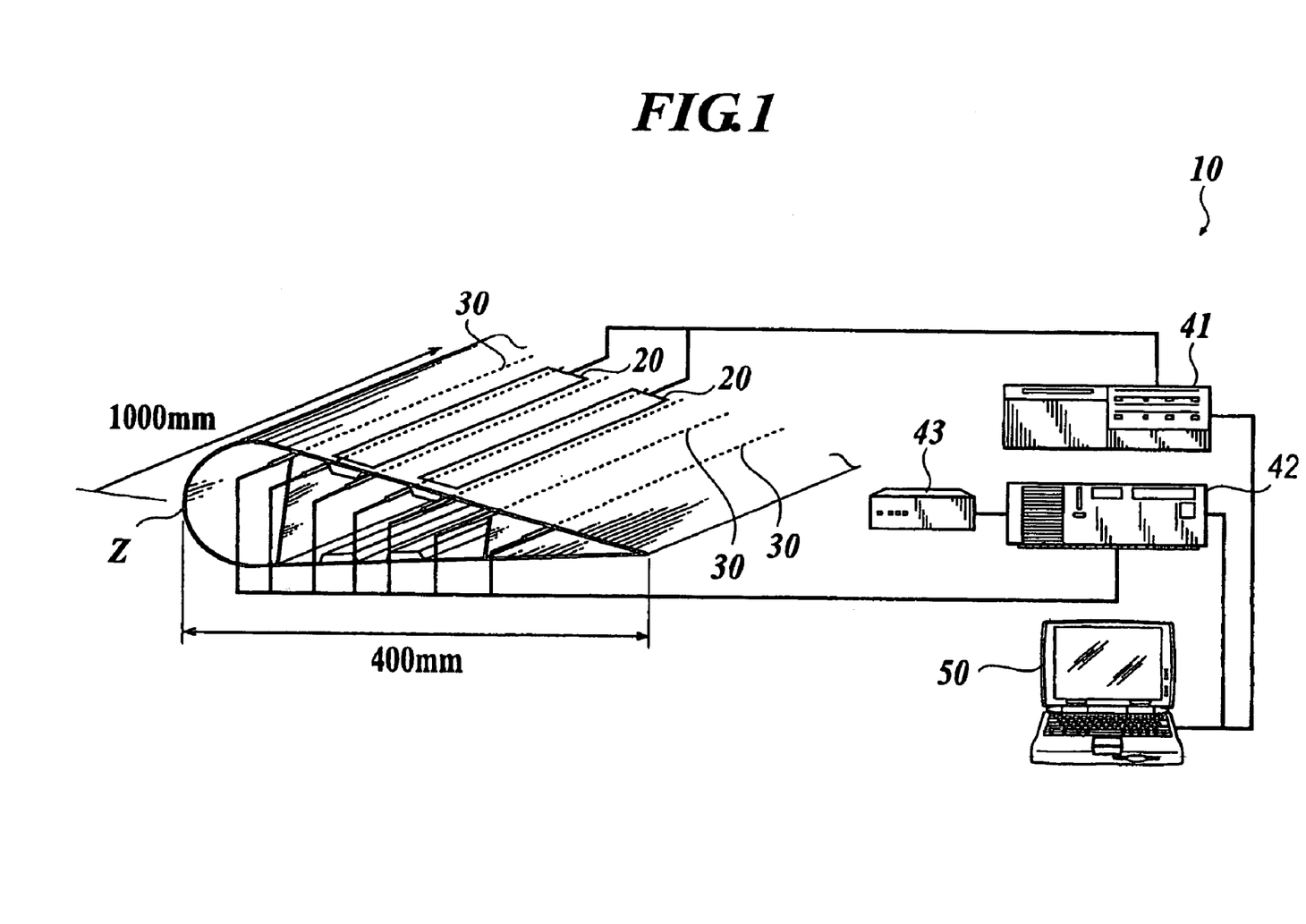
FIG. 1 is a schematic configuration view of a damage detection system which detects damage to a structural composite material according to an embodiment of the present invention.

A damage detection system 10 for a structural composite material, which is an embodiment of the present invention, will be described. FIG. 1 is a schematic configuration view of the damage detection system 10 which detects damage to a structural composite material Z.

Here, a case where the structural composite material Z is applied to a main wing of an aircraft is illustrated. The damage detection system 10 detects occurrence of damage to the structural composite material Z at points where damage should be detected.

(Entire Configuration of Damage Detection System)

As shown in FIG. 1, the damage detection system 10 for a structural composite material as the present embodiment, includes: a plurality of vibration application apparatuses 20 adhered to the surface of the structural composite material Z in the vicinities of points where damage detection for the structural composite material Z should be performed; a plurality of fiber optic sensors 30 installed in the vicinities of the points where damage detection for the structural composite material Z should be performed; a control apparatus 41 which controls a plurality of piezo elements 21 held by the respective vibration application apparatuses 20; a spectrum analyzer 42 as a characteristic detection unit which detects a change in characteristics of reflection light, which is obtained from the respective fiber optic sensors 30; and a detection processing apparatus 50 which determines whether damage exists or not based on outputs from the piezo elements 21 held by the respective vibration application apparatuses 20 and of the spectrum analyzer 42. Hereinbelow, the respective components will be detailed.

(Vibration Application Apparatus)

The vibration application apparatuses 20 have substantially the same structure as that of an apparatus used as a piezo sensor. As shown in the plan view in FIG. 2, each of the vibration application apparatuses 20 includes a sheet body 22, the plurality of piezo elements 21 sprinkled throughout and held by the sheet body 22, and a plurality of wires 23 for the piezo elements 21 provided to the sheet body 22.

Figure 2:
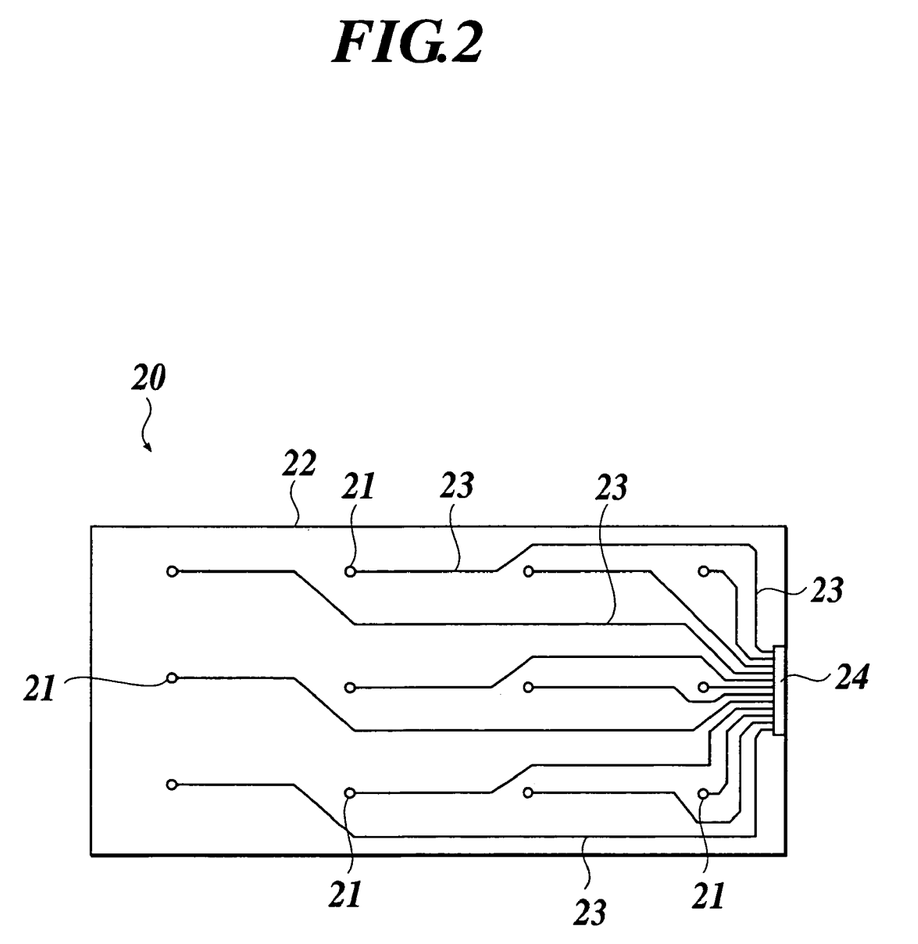
FIG. 2 is a plan view of a vibration application apparatus disclosed in FIG. 1.

The sheet body 22 is made of, for example, a polyimide, shaped like a film, and has flexibility and deformability. The sheet body 22 serves to hold the piezo elements 21 in order to keep a state where the plurality of sprinkled piezo elements 21 are in contact with the surface of the structural composite material Z, on which detection of damage and the like is performed.

The respective piezo elements 21 themselves are also shaped like a film, and disposed so as to be sprinkled on one side of the sheet body 22. The sheet body 22 is flat, and the piezo elements 21 are sprinkled all over the flat surface of the sheet body 22 so as not to be disproportionately placed thereon.

Film-shaped lead wires as the wires 23 are drawn from the respective piezo elements 21 along the surface of the sheet body 22 to be concentrated at a connector 24 provided on one end of the sheet body 22. Each of the wires 23 on the flat surface of the sheet body 22 are covered with an insulating coating from the top thereof, thereby insulated from each other as well as from outside.

When a driving voltage is applied from outside, the thickness of the piezo elements 21 is changed in the thickness direction. By utilizing such a characteristic, the control apparatus 41 can apply instantaneous vibration to the wall surface of the structural composite material Z by applying a driving pulse voltage to an arbitrary piezo element 21.

(Fiber Optic Sensor)

Figure 3A:
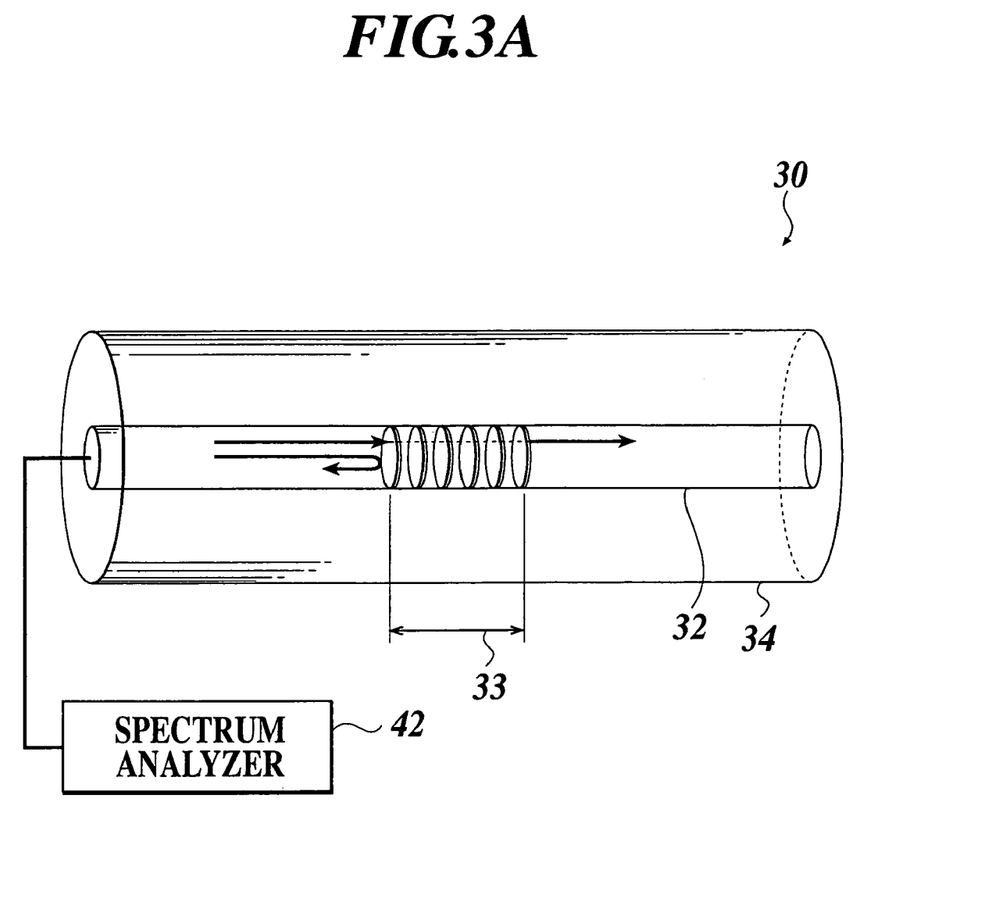
FIG. 3A is a schematic configuration view of a fiber optic sensor.

As shown in a schematic configuration view in FIG. 3A, each of the fiber optic sensors 30 includes an optical fiber 34 having, in a core portion 32 thereof, a grating portion 33 which reflects light of a predetermined wavelength.

For the optical fiber 34, an optical fiber with an outer diameter of approximately 50 to 100 μm is used. The outer diameter may be smaller, and the smaller the outer diameter is, the more suppressed the reduction in the strength of the structural composite material Z is, upon installation of the optical fiber 34.

The optical fiber 34 is connected to the spectrum analyzer 42 at one end thereof. Irradiation light that covers a wavelength bandwidth in a predetermined range is incident on the core portion 32 from a light source (not shown) included in the spectrum analyzer 42. The light that has entered the core portion 32 from the spectrum analyzer 42 propagates through the core portion 32, and light of a certain wavelength is reflected from the grating portion 33.

Figure 3B:
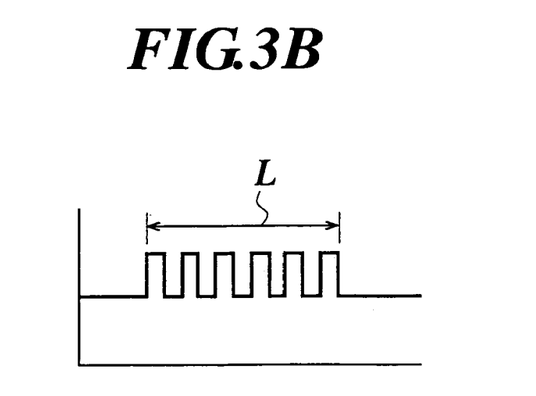
FIG. 3B is a diagram showing a refractive index change of a grating portion in the light traveling direction.

FIG. 3B is a diagram showing a refractive index change of the core portion 32 in the light traveling direction. The refractive index of the grating portion 33 is shown in a region L in the drawing.

As shown in the drawing, the grating portion 33 is formed such that the refractive index of the core portion 32 is periodically changed. The grating portion 33 is formed so as to selectively reflect light of a particular wavelength from the boundary where the refractive index is changed. The wavelength of reflection light is shifted when vibration is applied and disturbance such as distortion is caused to the grating portion 33. When a wavelength of reflection light is $\lambda_B$, a wavelength shift amount is $\Delta\lambda_B$, a photoelectric effect coefficient is $P\epsilon$, a strain amount of the grating portion 33 is $\epsilon$, a temperature coefficient is $\xi$, and a temperature change is $\Delta T$, the following relationship is established:

$$\Delta\lambda_B/\lambda_B = (1-P\epsilon)\cdot\epsilon + \xi\Delta T$$

Thus, when vibration is applied to the grating portion 33, the strain amount E of the grating portion 33 changes, and consequently, the wavelength of reflection light is shifted in accordance with the strain amount E. If vibration from a vibration source is transmitted well, the grating portion 33 is largely deformed, and the wavelength shift amount $\Delta\lambda_B$ becomes large. If vibration from the vibration source is not transmitted well, the grating portion 33 is strained a little, and the wavelength shift amount $\Delta\lambda_B$ becomes small.

(Spectrum Analyzer)

The spectrum analyzer 42 is capable of detecting light intensity distribution in a predetermined wavelength bandwidth. More specifically, a wavelength of reflection light can be detected by irradiating the core portion 32 of the fiber optic sensor 30 with light from the light source, and detecting light reflected from the grating portion 33. As described above, the grating portion 33 of the fiber optic sensor 30 reflects only light of a certain frequency, and the frequency is shifted in accordance with distortion of the grating portion 33. Hence, by detecting the frequency of light of a high intensity when vibration is applied, a frequency shift can be detected. The frequency shift detected by the spectrum analyzer 42 is subjected to A/D conversion through an interface (not shown) and outputted to the detection processing apparatus 50.

Reference numeral 43 shown in FIG. 1 denotes a power supply circuit of the spectrum analyzer 42.

(Control Apparatus)

The control apparatus 41 includes a function of applying a pulse voltage to a piezo element 21 specified by the detection processing apparatus 50, and driving the specified piezo element 21 to apply vibration to the structural composite material Z as a vibration generation unit.

(Detection Processing Apparatus)

Figure 4:
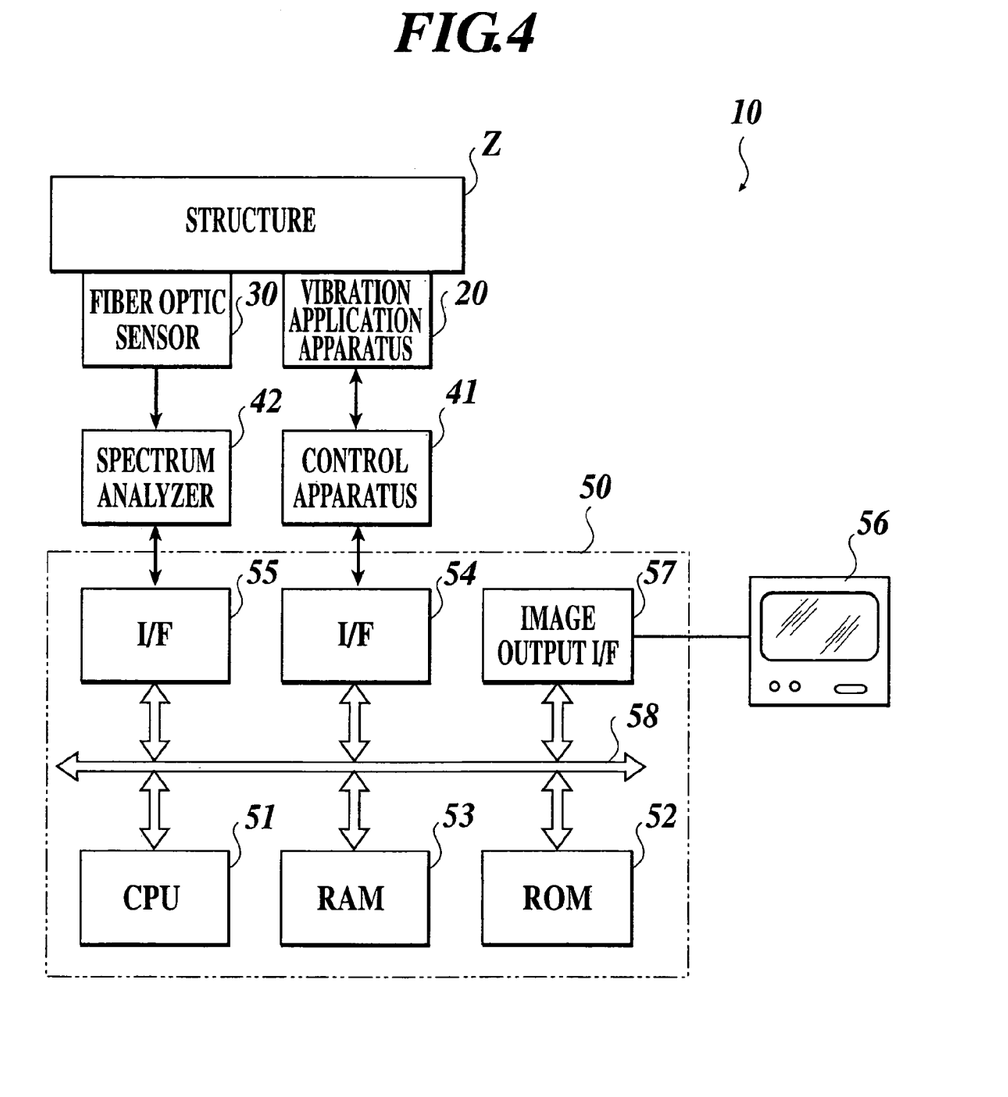
FIG. 4 is a block diagram showing a control system of the damage detection system for a structural composite material.

As shown in FIG. 4, the detection processing apparatus 50 includes: a CPU 51 which performs arithmetic processing in accordance with programs; a ROM 52 which stores the programs for various kinds of processing and control; a RAM 53 which serves as a work area where data and the like are temporarily stored during the various kinds of processing; an interface 54 which sends and receives data to and from the control apparatus 41 which controls the vibration application apparatuses 20; an interface 55 which sends and receives data to and from the spectrum analyzer 42; an image output interface 57 which converts detection result display data into an image signal that is appropriately formatted for a display monitor 56 and outputs the image signal to the display monitor 56; and a data bus 58 through which various instructions and data are transmitted among these units.

The damage detection system 10 applies vibration to the structural composite material Z through a piezo element 21 embedded at a predetermined position of a vibration application apparatus 20 provided on the structural composite material Z (in this embodiment, the main wing of an aircraft) on which damage detection is to be performed. The damage detection system 10 then detects whether damage exists or not in the vicinity of the fiber optic sensor 30 based on the propagation state of an elastic wave detected by the fiber optic sensor 30. The detection processing apparatus 50 executes various functions through the CPU 51 which processes, using the RAM 53, the various programs stored in the ROM 52. Hereinbelow, the various functions executed by the detection processing apparatus 50 will be described.

(1) In accordance with the programs stored in the ROM 52, the CPU 51 performs operation control of the control apparatus 41 so that the control apparatus 41 applies a driving pulse voltage to an arbitrary piezo element 21. Any of the plurality of piezo elements 21 may be selected; however, to use as a vibration-generating source, it is preferable to select, for example, a piezo element between which and the grating portion 33 of the fiber optic sensor 30 there is a portion of the composite material Z to which damage is easily caused.

Alternatively, the control programs of the CPU 51 may be set such that the piezo element 21 to which a driving pulse is applied is changed sequentially, and detection is performed for the respective piezo elements 21.

(2) In accordance with the programs stored in the ROM 52, the CPU 51 performs processing of obtaining detection data which shows a frequency distribution detected by the spectrum analyzer 42 after a driving pulse voltage is applied, and of storing in the RAM 53 the detection data on each of the fiber optic sensors 30. Moreover, based on the respective detection data, the CPU 51 creates waveform images which show the respective frequency distributions, and performs operation control of displaying the waveform images on the display monitor 56 through the image output interface 57.

(3) In accordance with the programs stored in the ROM 52, the CPU 51 performs processing of determining whether damage exists or not based on detection data stored in the RAM 53 which show the frequency characteristics of the respective fiber optic sensors 30. For such determination, for example, detection data on an ideal frequency distribution is obtained by applying vibration to the structural composite material Z without defect for a certain period of time from the start of vibration application under certain conditions, and the detection data is stored in the RAM 53 of the detection processing apparatus 50 beforehand. The detection data on the ideal frequency distribution is compared with the detection data on a frequency distribution obtained when damage is detected by applying vibration under the same conditions as the above. The comparison is as follows.

When there is no damage, vibration propagates well to the grating portion 33 of the fiber optic sensor 30. Therefore, the frequency of reflection light thus obtained is largely shifted from the frequency of reflection light obtained when no vibration is applied. On the other hand, when damage exists on the vibration propagation path, the path through which vibration is to propagate to the grating portion 33 of the fiber optic sensor 30 is changed. Thus, the frequency of reflection light in this case is different from the frequency of reflection light obtained when there is no vibration. The CPU 51 compares the frequency characteristic obtained when vibration is applied to the structural composite material Z having damage with the frequency characteristic obtained when vibration is applied to the structural composite material Z having no damage. The CPU 51 determines that damage exists when the result of comparison shows that the frequency characteristic has been changed by a predetermined degree or more.

Alternatively, through frequency spectrum analysis, the CPU 51 obtains a center frequency of reflection light obtained when no vibration is applied and a center frequency of reflection light obtained when vibration is applied. The CPU 51 then obtains the difference between these center frequencies by subtraction. The shift amount in the frequency distribution is thus obtained. The CPU 51 compares this shift amount with the shift amount in the frequency distribution of reflection light obtained when there is no damage, and determines that damage exists when the result of the comparison shows that the former shift amount is equal to or smaller than a predetermined amount.

Further, if it is determined in accordance with the comparison result that there is damage, the CPU 51 performs operation control of displaying, on the display monitor 56 through the image output interface 57, which of the fiber optic sensors 30 has shown the anomaly.

In the detection processing apparatus 50, the comparison is made using detection data on the healthy structural composite material Z obtained beforehand. However, the way of determining whether there is damage or not is not limited thereto. For example, a threshold value may be set for a shift value of a specific frequency in a frequency distribution detected by the spectrum analyzer 42 from the fiber optic sensor 30. The shift value is obtained by comparing a value of a specific frequency obtained when no vibration is applied and a value obtained when vibration is applied. It may be determined that there is damage when the shift value is equal to or less than the threshold value.

(Operation of Damage Detection System)

A description will be given of a damage detection operation on the main wing of an aircraft that is the structural composite material Z performed by the damage detection system 10 having the above components.

The main wing of an aircraft has a hollow structure, and spars are provided inside the main wing along the longitudinal direction. Since the respective vibration application apparatuses 20 are shaped like a sheet, relatively large holes for installation work through which the vibration application apparatuses 20 are passed need to be provided in order to install the vibration application apparatuses 20 inside the main wing of an aircraft with such a structure as described above. For this reason, the vibration application apparatuses 20 are adhered on the surfaces of the spars. The respective fiber optic sensors 30 are shaped like a fine cable. Since the fiber optic sensors 30 have a fine diameter, reduction in the strength of the main wing can be prevented even when the fiber optic sensors 30 are installed inside the main wing. Accordingly, the fiber optic sensors 30 are installed along the spars, etc. to which stress is to be particularly applied. It is preferable that at least the entire grating portion 33 is in tight contact with the composite material Z in view of the respective fiber optic sensors 30. The fiber optic sensors 30 are adhered to the surface of the inner wall surface of the main wing with an adhesive or a sticky tape. Alternatively, since the fiber optic sensors 30 have a fine diameter, the fiber optic sensors 30 may be embedded inside the wall surface integrally with fibers used as a material for the spars, etc., at the stage of forming the spars, etc.

A pulse voltage is applied to a predetermined piezo element 21, and the frequency of reflection light obtained when vibration is applied is detected by the spectrum analyzer 42 through the fiber optic sensor 30. Thus, determination is made as to whether damage exists between the piezo element 21 to which the vibration is applied and the grating portion 33 of the fiber optic sensor 30 and therearound.

The detection processing apparatus 50 determines whether there is damage or not, and outputs the determination result to the display monitor 56.

(Advantageous Effect of Damage Detection System)

In the damage detection system 10 for a structural composite material, used are the fiber optic sensors 30 using an optical fiber whose diameter can be made small. Hence, reduction in the strength of the structural composite material Z can be prevented even when the vibration application apparatuses 20 are installed, and the vibration application apparatuses 20 can be placed close to the points to which damage is easily caused. Accordingly, damage can be detected at an early stage with high accurately.

Vibration generated by an arbitrary piezo element 21 of a vibration application apparatus 20 is transmitted to the grating portion 33 of a fiber optic sensor 30, and damage is detected based on the frequency shift of reflection light. Thus, not only local damage around the fiber optic sensor 30, but also damage in a wider area on the vibration transmission path can be detected.

(Others)

In the above, pulse vibration is generated by one of the piezo elements 21 at the time of damage detection. However, it goes without saying that damage detection is not limited thereto, and vibration of a certain frequency may be generated for a certain period of time.

In the embodiment, a main wing of an aircraft has been used as an example of a structure made of a structural composite material. However, it goes without saying that the structure is not limited thereto.

Figure 5:
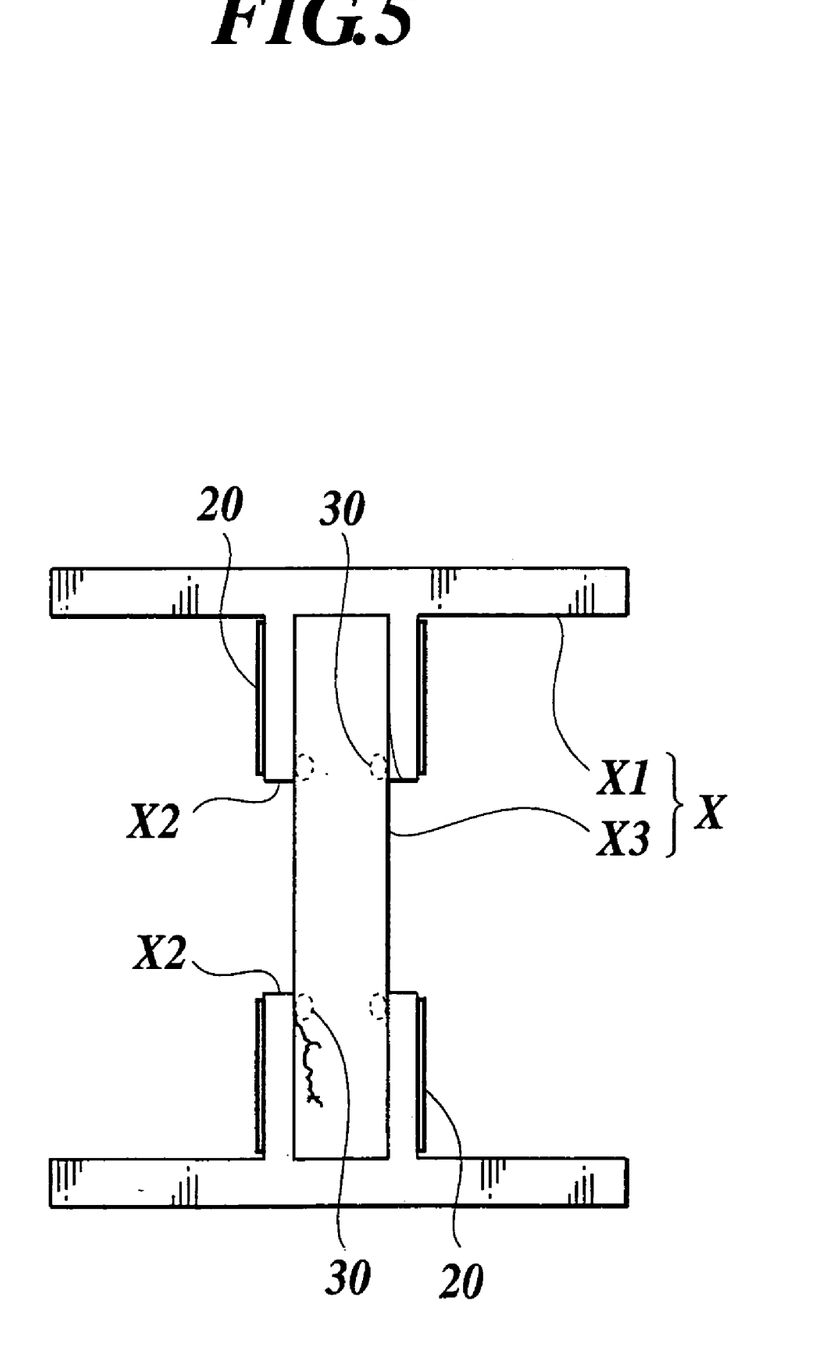
FIG. 5 is an explanatory view showing an example of installation of the fiber optic sensor and a vibration application apparatus when the damage detection system is applied to another structure.

For example, FIG. 5 shows a n-shaped structure X made of a composite material, in which flanges X2 are provided to each of a pair of upper and lower horizontal flat plates X1, and the top and bottom ends of a vertical web X3 in a flat plate shape are bonded to the respective flanges X2 to be sandwiched therebetween.

In a case where the damage detection system 10 is applied to the structure X, the fiber optic sensors 30 are embedded on the web X3 side of the bonded surfaces between the flanges X2 and the web X3, and the vibration application apparatuses 20 are adhered on the outer surfaces of the flanges X2. Thus, the boundary surfaces between the flanges X2 and the web X3, which surfaces are prone to damage, are placed between the vibration application apparatuses 20 and the fiber optic sensors 30 that is a vibration transmission path. Thus, damage is detected with high accuracy.

Here, there are cases where the web X3 is molded separately from the flanges X2 and then bonded to each other, and where the web and flanges are formed using fibers, then assembled, and integrally molded by resin transfer molding (RTM). The fiber optic sensors 30 are embedded upon lamination in the case of prepreg lamination, and upon lamination of the fibers in the case of RTM.

The fiber optic sensors 30 may be disposed in the joined portion between the web X3 and the flanges X2 to be sandwiched therebetween.

Figure 6:
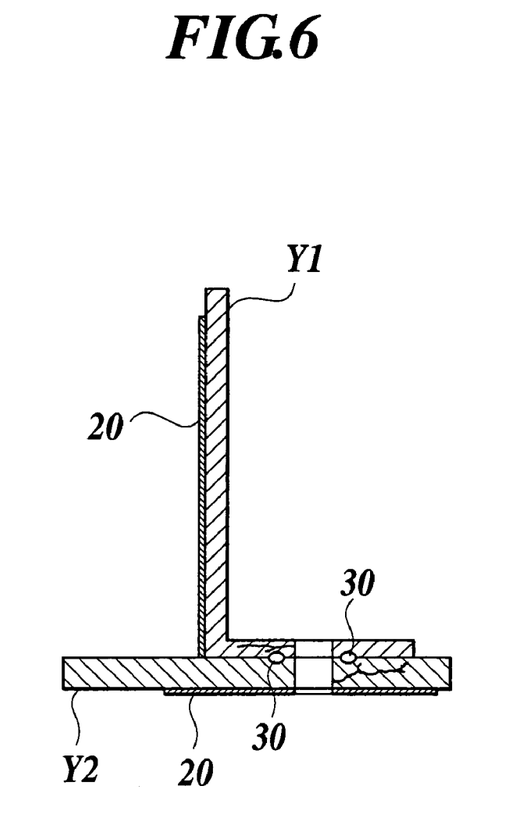
FIG. 6 is an explanatory view showing an example of installation of the fiber optic sensor and the vibration application apparatus when the damage detection system is applied to still another structure.

In FIG. 6, an L-shaped member Y1 and a flat plate Y2 which are made of a composite material are molded separately, and jointed to each other with screws or rivets by fastening. In this case, the fiber optic sensors 30 (with a fine diameter of Φ=0.052 mm) are embedded in the L-shaped member Y1 or the flat plate Y2, and subjected to mold curing. In other words, the fiber optic sensors 30 are embedded when the L-shaped member Y1 and the flat plate Y2 which are prepreg laminations are laminated, or when the fibers are laminated in the case of RTM.

Here, it is preferable that the fiber optic sensor(s) 30 are embedded in one of the members, and the vibration application apparatus 20 is placed on the other member so as to be on the opposite side with respect to the above member. Thus, the boundary surface between the L-shaped member Y1 and the flat plate Y2, which surface is prone to damage, is placed between the vibration application apparatuses 20 and the fiber optic sensor(s) 30, which is the vibration transmission path, whereby damage is detected with high accuracy.

Also in this case, the fiber optic sensors 30 may be disposed in the joined portion between the L-shaped member Y1 and the flat plate Y2 so as to be sandwiched therebetween, as shown in FIG. 6.

Figure 7:
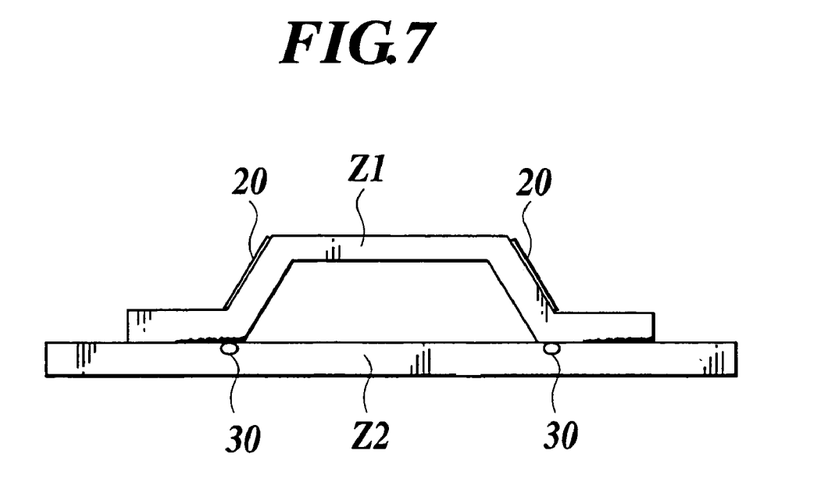
FIG. 7 is an explanatory view showing an example of installation of the fiber optic sensor and the vibration application apparatus when the damage detection system is applied to yet another structure.

FIG. 7 shows a structure including a hat member Z1 and a flat plate Z2 which are made of a composite material. There are cases where the hat member Z1 and the flat plate Z2 are separately molded and then bonded to each other, and where the hat member Z1 and the flat plate Z2 are formed using fibers, then assembled, and integrally molded by RTM with a split mold disposed therebetween.

Also in this case, the fiber optic sensors 30 (with a fine diameter of Φ=0.052 mm) are embedded in the hat member Z1 or the flat plate Z2, and subjected to mold curing. In other words, the fiber optic sensors 30 are embedded when the hat member Z1 and the flat plate Z2 which are prepreg laminations are laminated, or when the fibers are laminated in the case of RTM. Otherwise the fiber optic sensors 30 are bonded between the hat member Z1 and the flat plate Z2.

Also in this case, it is preferable that the fiber optic sensors 30 are embedded in one of the members and the vibration application apparatuses 20 are placed on the other member so as to be on the opposite side with respect to the above member. Thus, the boundary surface between the hat member Z1 and the flat plate Z2, which surface is prone to damage such as delamination and disbanding, is placed between the vibration application apparatuses 20 and the fiber optic sensors 30 that is the vibration transmission path, whereby damage is detected with high accuracy.

Also in this case, the fiber optic sensors 30 may be disposed in the bonded portion between the hat member Z1 and the flat plate Z2 so as to be sandwiched therebetween.

The entire disclosure of Japanese Patent Application No. Tokugan 2003-335108 filed on Sep. 26, 2003 including specification, claims, drawings and summary are incorporated herein by reference in its entirety.

What is claimed is:

1. A damage detection system for a structural composite material, comprising:
   a piezo element;
   a fiber optic sensor which includes a grating portion in a core portion thereof, the grating portion configured to reflect light of a predetermined wavelength;
   a light source configured to perform light irradiation onto the core portion; and
   a characteristic detection unit configured to detect a characteristic of the light reflected from the grating portion,
   wherein the structural composite material includes a plurality of members that are joined to each other at a joining portion, and
   wherein the fiber optic sensor is placed in the joining portion so as to be sandwiched between the members.

2. The damage detection system as claimed in claim 1, wherein the piezo element is disposed in a vicinity of the joining portion.

3. The damage detection system as claimed in claim 2, wherein the piezo element and the fiber optic sensor are disposed such that one of the members is placed therebetween.

4. A damage detection method for a structural composite material, comprising
   providing:
      the structural composite material comprising a plurality of members that are joined to each other at a joining portion,
      a piezo element fixedly disposed at a vicinity of the joining portion,
      a lead wire which transmits a signal to the piezo elements,
      a fiber optic sensor which is fixedly disposed in the joining portion so as to be sandwiched between the members and includes a grating portion in a core portion, the grating portion reflecting light of a predetermined wavelength,
      a light source which performs light irradiation onto the core portion, and
      a characteristic detection unit which detects a characteristic of the light reflected from the grating portion;
   applying vibration to the structural composite material by using the piezo element; and
   detecting damage based on a change in an output from the characteristic detection unit.

5. A damage detection system for a structural composite material, comprising:
   a vibration application apparatus configured to apply vibration to the structural composite material;
   a fiber optic sensor which includes a grating portion in a core portion thereof, the grating portion configured to reflect light of a predetermined wavelength;
   a light source to configured to perform light irradiation onto the core portion; and
   a characteristic detection unit configured to detect a characteristic of the light reflected from the grating portion,
   wherein the vibration application apparatus comprises a plurality of piezo elements,
   wherein the structural composite material includes a plurality of members that are joined to each other at a joining portion, and
   wherein the fiber optic sensor is placed in the joining portion so as to be sandwiched between the members.

6. The damage detection system as claimed in claim 5, wherein the vibration application apparatus further comprises:
   a sheet body, wherein the plurality of piezo elements are sprinkled throughout and held by the sheet body; and
   a plurality of wires for the piezo elements provided to the sheet body.

7. The damage detection system as claimed in claim 6, wherein the sheet body has flexibility and deformability.

8. The damage detection system as claimed in claim 5, wherein the fiber optic sensor has an outer diameter of 50 to 100 μm.

9. The damage detection system as claimed in claim 5, wherein the fiber optic sensor has an outer diameter of less than 50 μm.

10. The damage detection system as claimed in claim 5, wherein vibration applied from the vibration application apparatus is transmitted to the fiber optic sensor through the structural composite material.

11. The damage detection system as claimed in claim 10, wherein the vibration applied from the vibration application apparatus is instantaneous vibration.

12. The damage detection system as claimed in claim 5, wherein the vibration application apparatus is provided on the surface of the structural composite material.

13. The damage detection system as claimed in claim 12, wherein the vibration application apparatus is provided by adhesion or bonding.

14. The damage detection system as claimed in claim 5, wherein the fiber optic sensor is provided inside a hollow in the structural composite material.

15. The damage detection system as claimed in claim 5, wherein the structural composite material includes a plurality of members which are joined to each other at a joining portion, and the vibration application apparatus and the fiber optic sensor are disposed in or in the vicinity of the joining portion.

16. The damage detection system as claimed in claim 15, wherein the fiber optic sensor is placed in the joining portion so as to be sandwiched between the members, or embedded in one of the members so as to be placed in the vicinity of the joining portion.

17. The damage detection system as claimed in claim 15, wherein the vibration application apparatus and the fiber optic sensor are disposed such that one of the members is placed therebetween.

18. A damage detection system for a structural composite material, comprising:
   a piezo element;
   a fiber optic sensor which includes a grating portion in a core portion thereof, the grating portion configured to reflect light of a predetermined wavelength;
   a light source configured to perform light irradiation onto the core portion; and
   a characteristic detection unit configured to detect a characteristic of the light reflected from the grating portion,
   wherein the structural composite material includes a plurality of members that are joined to each other at a joining portion, and
   wherein the fiber optic sensor is embedded in one of the members so as to be placed in a vicinity of the joining portion.

19. The damage detection system as claimed in claim 18, wherein the piezo element is disposed in the vicinity of the joining portion.

20. The damage detection system as claimed in claim 1, wherein the piezo element is installed such that a vibration propagation path from the piezo element to the grating portion passes through the joining portion.

21. The damage detection system as claimed in claim 18, wherein the piezo element is installed such that a vibration propagation path from the piezo element to the grating portion passes through the joining portion.

22. The damage detection system as claimed in claim 1,
   wherein the piezo element is disposed on a first surface of the structural composite material, and
   wherein the fiber optic sensor is disposed on a second surface of the structural composite material different from the first surface.

23. The method as claimed in claim 4, wherein the providing step further comprises:
   disposing the piezo element on a first surface of the structural composite material; and
   disposing the fiber optic sensor on a second surface of the structural composite material different from the first surface.

24. The damage detection system as claimed in claim 12, wherein the fiber optic sensor is provided on a surface of the structural composite material that is different from the surface of the structural composite material on which the vibration application apparatus is provided.

25. The damage detection system as claimed in claim 18,
   wherein the piezo element is disposed on a first surface of the structural composite material, and
   wherein the fiber optic sensor is disposed on a second surface of the structural composite material different from the first surface.

26. The damage detection system as claimed in claim 22, wherein the first and second surfaces are opposite surfaces of the structural composite material.

27. The method as claimed in claim 23, wherein the first and second surfaces are opposite surfaces of the structural composite material.

28. The damage detection system as claimed in claim 24, wherein the surface on which the fiber optic sensor is provided and the surface on which the vibration application apparatus is provided are opposite surfaces of the structural composite material.

29. The damage detection system as claimed in claim 25, wherein the first and second surfaces are opposite surfaces of the structural composite material.

* * * * *